(12) United States Patent
Chen

(10) Patent No.: US 10,105,084 B2
(45) Date of Patent: Oct. 23, 2018

(54) BLOOD SAMPLER

(71) Applicant: JIERYANG BIOTECH, INC., Taichung (TW)

(72) Inventor: Chih-Fu Chen, Taichung (TW)

(73) Assignee: JIERYANG BIOTECH, INC., Taichung (TW)

( * ) Notice: Subject to any disclaimer, the term of this patent is extended or adjusted under 35 U.S.C. 154(b) by 285 days.

(21) Appl. No.: 15/008,824

(22) Filed: Jan. 28, 2016

(65) Prior Publication Data
US 2017/0215781 A1    Aug. 3, 2017

(51) Int. Cl.
*A61B 5/15*    (2006.01)

(52) U.S. Cl.
CPC .. *A61B 5/150343* (2013.01); *A61B 5/150236* (2013.01); *A61B 5/150244* (2013.01); *A61B 5/150351* (2013.01)

(58) Field of Classification Search
CPC ............. A61B 5/150236; A61B 5/150244
See application file for complete search history.

(56) References Cited

U.S. PATENT DOCUMENTS

| | | | | |
|---|---|---|---|---|
| 5,114,404 A | * | 5/1992 | Paxton | A61M 5/315 604/110 |
| 5,454,793 A | * | 10/1995 | Levander | A61M 5/24 604/207 |
| 6,123,687 A | * | 9/2000 | Simonyi | B01D 21/245 604/207 |
| 8,038,656 B2 | * | 10/2011 | Lloyd | A61M 5/31515 604/218 |
| D712,025 S | * | 8/2014 | Kawamura | D24/112 |
| 9,326,914 B2 | * | 5/2016 | Anitua Aldecoa | A61B 5/1433 |
| 9,329,165 B2 | * | 5/2016 | Ihm | B01L 3/5021 |
| 2004/0153034 A1 | * | 8/2004 | Fan | A61M 5/322 604/197 |
| 2004/0167004 A1 | * | 8/2004 | Jorgensen | A61M 1/029 494/37 |
| 2006/0106341 A1 | * | 5/2006 | Lou | A61M 5/322 604/110 |
| 2010/0025342 A1 | * | 2/2010 | Morimoto | A61B 5/1416 210/787 |
| 2010/0234799 A1 | * | 9/2010 | Paris | A61C 5/62 604/82 |

(Continued)

*Primary Examiner* — Sean Dougherty
(74) *Attorney, Agent, or Firm* — Muncy, Geissler, Olds & Lowe, P.C.

(57) ABSTRACT

A blood sampler includes a hollow transparent barrel including a reduced collection portion located at a front end thereof and terminating in a reduced coupling portion, an outlet defined in the coupling portion and a plurality of ribs spaced around and raised from an inside wall near an opposing rear end thereof, a piston axially movably fitted into the hollow transparent barrel and having a screw hole and peripheral ribs, a cap detachably capped onto the collection portion to seal the outlet, and a plunger having a screw rod located at a front end thereof and threaded into the screw hole of the piston for allowing movement the piston with the plunger. The hollow transparent barrel enables collecting blood sample from a patient, separating the collected blood sample into platelet-rich plasma, platelet-rich plasma and serum in a centrifuge and injecting the collected platelet-rich plasma into a patient body.

5 Claims, 13 Drawing Sheets

(56) References Cited

U.S. PATENT DOCUMENTS

2014/0276442 A1\* 9/2014 Haughey ............ A61M 5/31596
  604/191
2014/0276592 A1\* 9/2014 Mottola ............ A61M 5/31505
  604/506

\* cited by examiner

BLOOD SAMPLER

BACKGROUND OF THE INVENTION

1. Field of the Invention

The present invention relates to blood sampling technology and more particularly, to a blood sampler, which provides blood sample collection, blood sample centrifugation and hypodermic injection functions.

2. Description of the Related Art

Although blood is mainly a liquid called plasma, it also contains red cells, white cells, and platelets. The red blood cells are for delivering oxygen to all parts of the body. The white blood cells are a part of the immune system and help the body tight infection. The platelets are best known for their importance in clotting blood. However, platelets also contain hundreds of proteins called growth factors which are very important in the healing of injuries. Platelets stop bleeding by clumping and clogging blood vessel injuries. When platelets get to the site of the injury, they grow sticky tentacles that help them adhere. They also send out chemical signals to attract more platelets to pile onto the clot in a process called aggregation. Tissue repair begins with clot formation and platelet degranulation, which release the growth factors (GFs) necessary for wound repair. Except orthopedic treatment, RP (Platelet-rich plasma) technology has also been used in the treatment of diabetic foot, pressure ulcers and other chronic wound care, ophthalmic will use this autologous plasma for treatment of corneal ulcers or dry eye.

Since the platelets derived from the bone marrow are rich in growth factors that are the most easily accessible of human growth factors and can be used to promote angiogenesis and tissue regeneration and repair. However, because blood plasma also contains with red blood cells and white blood, the concentration of platelets in blood plasma is not enough for tissue repair. To develop a PRP preparation, blood must first be drawn from a patient. The platelets are separated from other blood cells through a centrifugation process, and their concentration is increased. Then the increased concentration of platelets can then be injected into the body to promote tissue regeneration and repair.

In operation, it needs to drain blood from the vein using a syringe with a blood injection needle, and then to inject collected blood into a test tube, and then to seal the test tube with a rubber cap and then put the test tube in a centrifuge for separation. After the centrifugation process, blood is separated into blood plasma at the bottom, platelet-rich plasma on the middle and serum in the upper phase. At this time, the medicare personnel needs to use another syringe and blood injection needle set and to insert the blood injection needle through the rubber cap of the test tube and the serum in the test tube into the platelet-rich plasma and to draw the platelet-rich plasma out of the test tube into the syringe. Because the amount of the serum in the test tube is higher than the amount of the platelet-rich plasma, a small amount of the serum can be drawn into the syringe when collecting the platelet-rich plasma. More particularly, if the length of the blood injection needle is not enough, the collected platelet-rich plasma can be mixed with a certain amount of the serum, lowering the concentration of the platelet-rich plasma and rendering an adverse effect on the tissue repair.

More particularly, in the process of autologous blood transfusion of collection of blood from a single patient and retransfusion back to the same patient, a first syringe and blood injection needle set is used to draw blood from the patient and to inject the collected blood into a test tube that is then sealed and put in a centrifuge for separation, enabling the collected blood to be separated into blood plasma at the bottom, platelet-rich plasma on the middle and serum in the upper phase. Thereafter, a second syringe and blood injection needle is used to draw the middle layer of platelet-rich plasma out of the test tube and then to inject the platelet-rich plasma into the injured are of the body of the patient. Because syringes, blood injection needle and test tube are disposable medical supplies, these disposable medical supplies must be undergo environmental treatment to prevent pollution. In the aforesaid process of autologous blood transfusion of collection of blood from a single patient and retransfusion back to the same patient, two syringe and blood injection needle sets and one test tube are used, wasting medical supplies. Further, the procedure is complicated.

There is known a vacuum blood sampler available on the market. The vacuum blood sampler comprises a holder 1, a blood collection needle 2, and a vacutainer tube 3. The blood collection needle 2 is fastened to one end of the holder 1. The vacutainer tube 3 has a stopper 4 fastened to a front end thereof. After insertion of the vacutainer tube 3 into the holder 1, the sharp rear end of the blood collection needle 2 is inserted through the stopper 4 into the inside of the vacutainer tube 3. When sampling blood of a patient, insert the blood collection needle 2 into the patient's vein, and then pull and push the vacutainer tube 3, drawing blood out of the patient's vein into the vacutainer tube 3. After removal of the vacutainer tube 3 from the holder 1, the stopper 4 seals the collected blood in the vacutainer tube 3. The vacutainer tube 3 is then transferred to a centrifuge for enabling the collected blood to be separated into plasma, platelet-rich plasma and serum. In application, a hypodermic syringe is used with a new blood injection needle draw the platelet-rich plasma from the vacutainer tube 3 and then to inject the platelet-rich plasma into the wound area of the patient. This method needs to use a vacuum blood sampler consisting of a holder 1, a blood collection needle 2 and a vacutainer tube 3 for collecting blood from the patient and separating platelet-rich plasma from the collected blood, and then to use a hypodermic syringe with a new blood injection needle for injecting the platelet-rich plasma into the wound area of the patient. This procedure is complicated, wastes medical supplies, and brings a waste material recycling problem.

SUMMARY OF THE INVENTION

The present invention has been accomplished under the circumstances in view. It is the main object of the present invention to provide a blood sampler, which provides blood sample collection, blood sample centrifugation and hypodermic injection functions and achieves the purposes of simplifying medical procedures and saving medical equipment.

To achieve this and other objects of the present invention, a blood sampler comprises a hollow transparent barrel, a piston, a cap, and a plunger. The hollow transparent barrel comprises a collection portion of reduced diameter axially forwardly extended from a front end thereof and terminating in a coupling portion in reduced diameter, an outlet axially extending through the collection portion and the coupling portion in communication between the inside space of the hollow transparent barrel and the atmosphere, and a plurality of longitudinal ribs spaced around an inside wall thereof and disposed near an opposite rear end thereof remote from the coupling portion. The piston is press-fitted into the inner diameter of the hollow transparent barrel, comprising a screw hole axially disposed in an inner side thereof remote from the coupling portion and a plurality of notches equiangularly spaced around the periphery thereof and adapted for mating with the ribs of the hollow transparent barrel. The cap comprises a blind hole detachably press-fitted onto the collection portion of the hollow transparent barrel to seal the outlet. The plunger is adapted for moving the piston relative to the hollow transparent barrel, comprising a screw rod located at a front end thereof and threaded into the screw hole of the piston.

Preferably, the hollow transparent barrel further comprises two annular stop flanges raised from the inside wall thereof adjacent to the longitudinal ribs for stopping the piston inside the hollow transparent barrel upon backward movement of the plunger to move the piston relative to the hollow transparent barrel.

Preferably, the cap further comprises a pin located at a bottom end of the blind hole and adapted for fitting into the outlet of the hollow transparent barrel to seal the outlet.

Preferably, the piston is an elastically deformable plastic member. The hollow transparent barrel further comprises a ring cap threaded onto an opposing rear end thereof. The ring cap comprises a transverse end wall for stopping the piston inside the hollow transparent barrel, and a through hole located at the center of the transverse end wall for the passing of the plunger.

Preferably, the plunger further comprises a thumb rest located at an opposite end thereof.

Thus, when drawing blood from a patient, attach a hub of a blood collection needle to the coupling portion of the hollow transparent barrel, and then thread the screw rod of the plunger into the screw hole of the piston, and then operate the thumb rest of the plunger to move the piston forwardly toward the collection portion of the hollow transparent barrel to further force the internal air out of the hollow transparent barrel, and then insert the pointed tip of the blood collection needle into the patient's vein, and then pull back the plunger to draw blood out of the patient's vein into the hollow transparent barrel. After a certain amount of blood has been drawn into the hollow transparent barrel, remove the blood collection needle from the patient's body and then cap the cap onto the collection portion of the hollow transparent barrel to force the pin of the cap into the outlet in the coupling portion, and thus, the outlet is sealed, thereafter, rotate the plunger to disengage the screw rod from the screw hole, thereby separating the plunger from the hollow transparent barrel and leaving the piston in the hollow transparent barrel to seal the collected blood sample in the hollow transparent barrel. Thereafter, put the hollow transparent barrel in a centrifuge with the cap facing down, enabling the blood sample to be separated into blood plasma at the bottom, the ratio of the minimum amount of platelet-rich plasma on the middle and serum in the upper phase, i.e., platelet-rich plasma is suspended between blood plasma and serum and, the amount of platelet-rich plasma is less than the amount of blood plasma and the amount of serum.

When going to inject the collected platelet-rich plasma into an injured area of a patient to help tissues heal, push the thumb rest of the plunger to move the piston toward the coupling portion to further squeeze the blood plasma out of the hollow transparent barrel, thereafter, attach the hub of a new blood collection needle to the coupling portion of the hollow transparent barrel, and then inject the blood collection needle into the injured area of the patient.

Thus, the hollow transparent barrel can be used for collecting blood sample and injecting platelet-rich plasma, and can also be used as a test tube for separating the collected blood sample into blood plasma, platelet-rich plasma and serum, allowing use of one common container in blood sample collection, blood sample centrifugation and platelet-rich plasma injection procedures, and thus, the invention achieves the purposes of simplifying medical procedures, shorting operating time and saving medical equipment.

Other advantages and features of the present invention will be fully understood by reference to the following specification in conjunction with the accompanying drawings, in which like reference signs denote like components of structure.

DETAILED DESCRIPTION OF THE INVENTION

Figure 1:
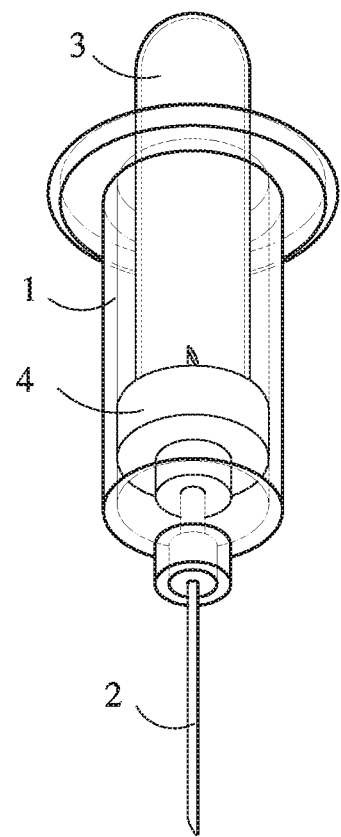
FIG. 1 is an exploded view of a vacuum blood sampler according to the prior art.
Figure 2:
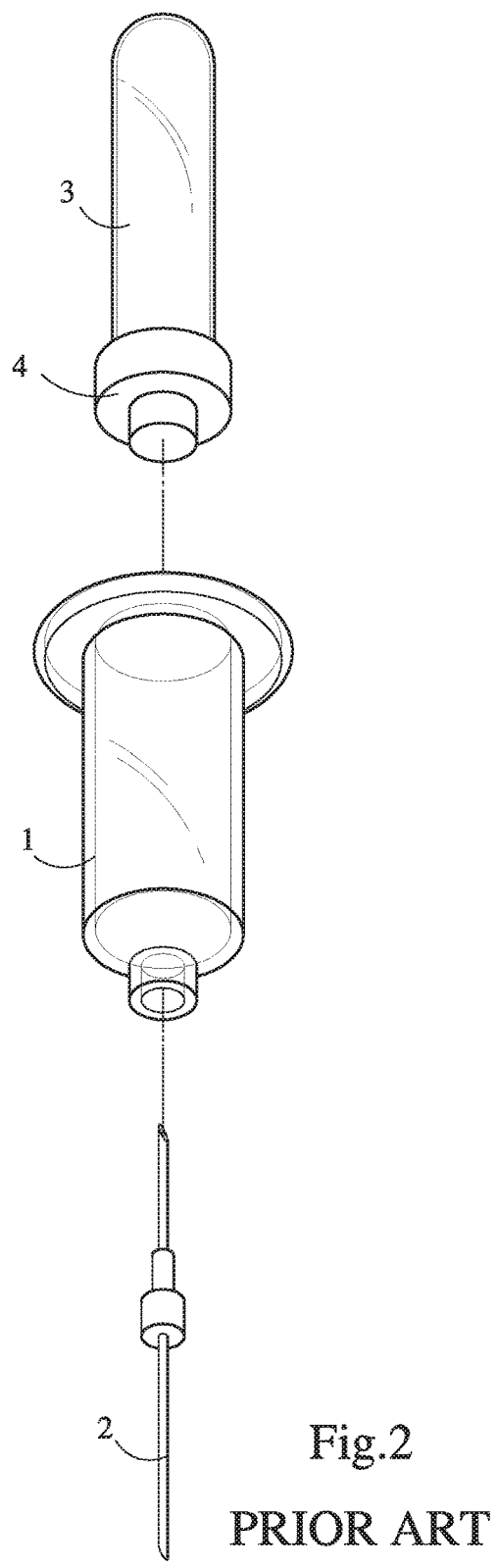
FIG. 2 is an exploded view of the vacuum blood sampler according to the prior art.
Figure 3:
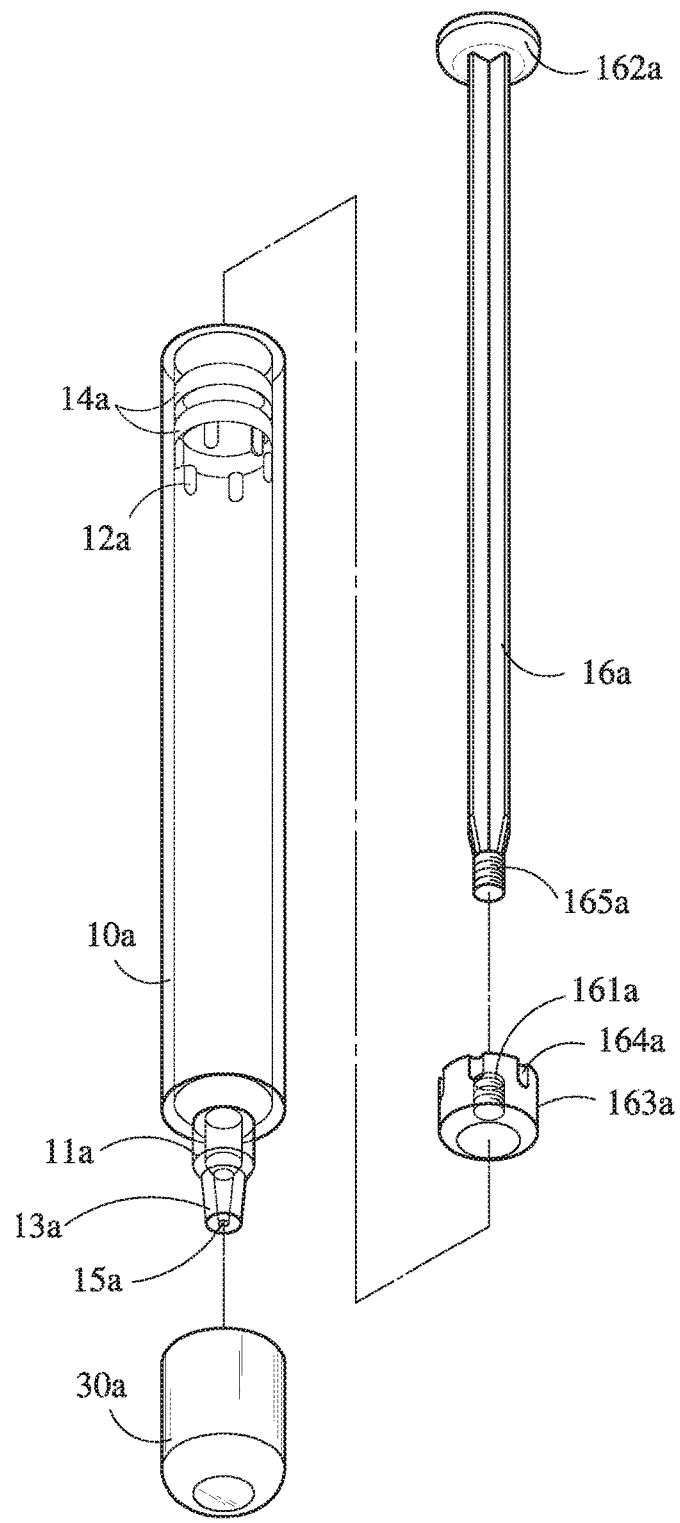
FIG. 3 is an exploded view of a blood sampler in accordance with a first embodiment of the present invention.
Figure 4:
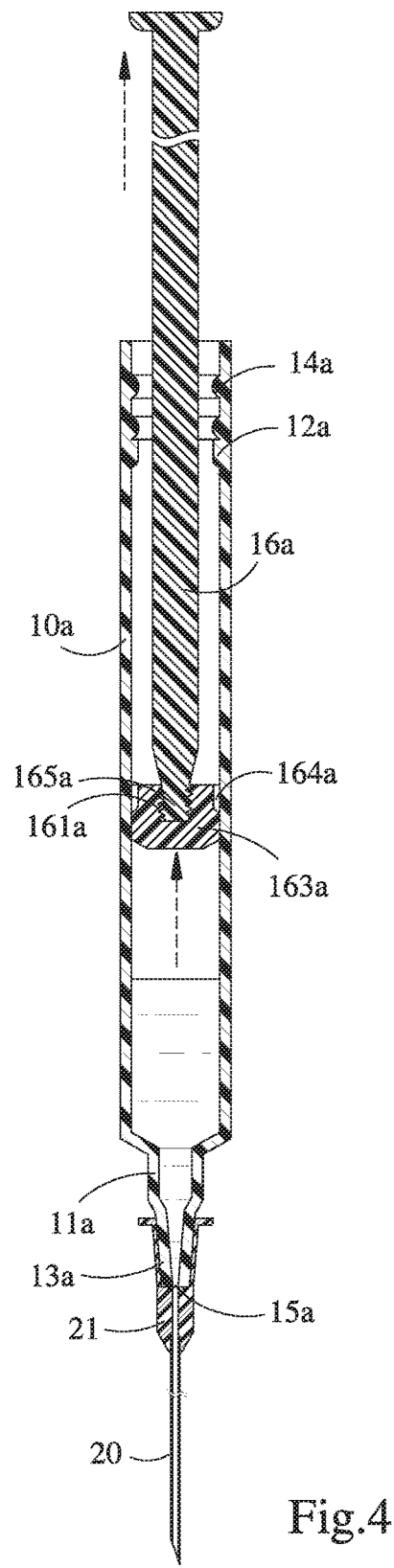
FIG. 4 is a schematic sectional applied view of the first embodiment of the present invention, illustrating a blood sampling operation of the blood sampler.

Referring to FIGS. 3 and 4, a blood sampler in accordance with a first embodiment of the present invention are shown. The blood sampler comprises a hollow transparent barrel 10a, a cap 30a, and a plunger 16a.

The hollow transparent barrel 10a comprises a collection portion 11a of reduced diameter axially forwardly extended from a front end thereof and terminating in a coupling portion 13a in reduced diameter, a plurality of longitudinal ribs 12a spaced around an inside wall thereof and disposed near an opposite rear end thereof remote from the coupling portion 13a, two annular stop flanges 14a raised from the inside wall adjacent to the longitudinal ribs 12a, and an outlet 15a axially extending through the collection portion 11a and the coupling portion 13a in communication between the inside space of the hollow transparent barrel 10a and the atmosphere. The hollow transparent barrel 10a further has a piston 163a axially movably mounted therein. The piston 163a is an elastically deformable plastic member fitted into the inner diameter of the hollow transparent barrel 10a, comprising a screw hole 161a axially disposed in an inner side thereof remote from the coupling portion 13a and a plurality of notches 164 equiangularly spaced around the periphery thereof corresponding to the ribs 12a of the hollow transparent barrel 10a.

The cap 30a comprises a blind hole 31a adapted for fitting onto the collection portion 11a of the hollow transparent barrel 10a, and a pin 32a located at a bottom end of the blind hole 31a and adapted for fitting into the outlet 15a in the coupling portion 13a to seal the outlet 15a.

The plunger 16a comprises a screw rod 165a located at one end thereof and threaded into the screw hole 161a of the piston 163a, and a thumb rest 162a located at an opposite end thereof for the rest of the thumb for enabling the hand to pull and push the plunger 16a relative to the hollow transparent barrel 10a conveniently and positively.

Figure 5:
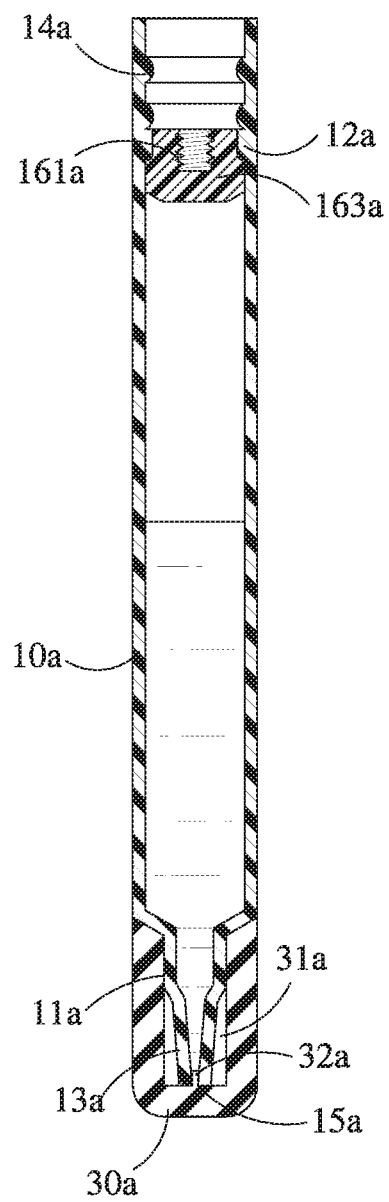
FIG. 5 is a schematic sectional view of the first embodiment of the present invention, illustrating a blood sample collected in the hollow transparent barrel.

Referring to FIG. 4 again, when drawing blood from a patient, thread-connect the piston 163a and the plunger 16a at first, and then attach a hub 21 of a blood collection needle 20 to the coupling portion 3a of the hollow transparent barrel 10a, and then operate the plunger 16a to push the thumb rest 162a in moving the piston 163a forwardly over the annular stop flanges 14a toward the collection portion 11a of the hollow transparent barrel 10a. After moved over the annular stop flanges 14a, the piston 163a is stopped from falling out of the hollow transparent barrel 10a. When pushing the thumb rest 162a of the plunger 16a to move the piston 163a forwardly toward the collection portion 11a of the hollow transparent barrel 10a, the internal air is forced out of the hollow transparent barrel 10a. At this time, insert the pointed tip of the blood collection needle 20 into the patient's vein, and then pull back the plunger 16a to draw blood out of the patient's vein into the hollow transparent barrel 10a. After a certain amount of blood has been drawn into the hollow transparent barrel 10a, remove the blood collection needle 20 from the patient's body and then cap the cap 30a onto the collection portion 11a of the hollow transparent barrel 10a to force the pin 32a of the cap 30a into the outlet 15a in the coupling portion 13a, and thus, the outlet 15a is sealed, as shown in FIG. 5. Thereafter, pull the plunger 16a to move the piston 163a backwardly to the position where the notches 164a of the piston 163a are respectively forced into engaged with the respective ribs 12a of the hollow transparent barrel 10a, and then rotate the plunger 16a to disengage the screw rod 165a from the screw hole 161a, thereby separating the plunger 16a from the hollow transparent barrel 10a and leaving the piston 163a in the hollow transparent barrel 10a.

Figure 6:
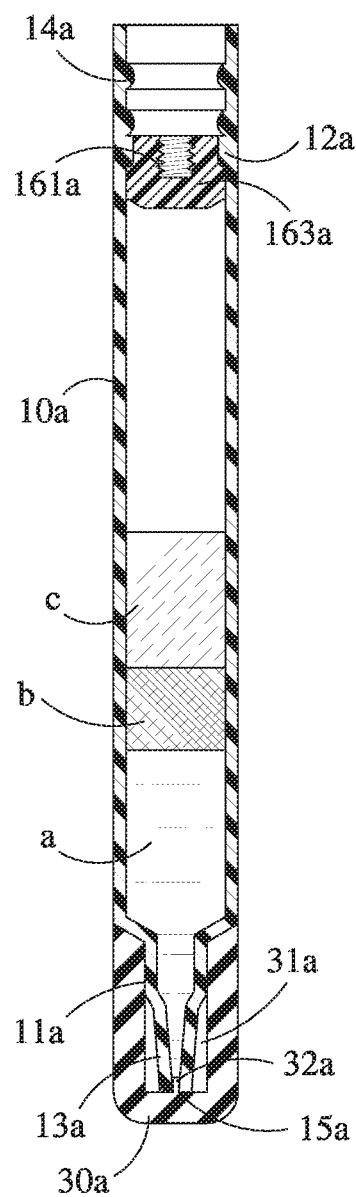
FIG. 6 is a schematic sectional view of the first embodiment of the present invention, illustrating the collected blood sample separated into blood plasma, platelet-rich plasma and serum.

Thereafter, put the hollow transparent barrel 10a in a centrifuge with the cap 30a facing down, enabling the blood sample to be separated into blood plasma (a) at the bottom, the ratio of the minimum amount of platelet-rich plasma (b) on the middle and serum (c) in the upper phase, as shown in FIG. 6. When going to inject the collected platelet-rich plasma (b) into an injured area of a patient to help tissues heal, keep the notches 164a of the piston 163a in engagement with respective ribs 12a of the hollow transparent barrel 10a, and then thread the screw rod 165a of the plunger 16a into the screw hole 161a of the piston 163a, and then push the thumb rest 162a of the plunger 16a to move the piston 165a toward the coupling portion 13a and to further squeeze the blood plasma (a) out of the hollow transparent barrel 10a, thereafter, attach the hub 21 of a new blood collection needle 20 to the coupling portion 13a of the hollow transparent barrel 10a, and then insert the blood collection needle 20 into the injured area of the patient, and then push the thumb rest 162a of the plunger 16a to move the piston 161a in forcing the platelet-rich plasma (b) out of the hollow transparent barrel 10a into the injured area of the patient.

Figure 7:
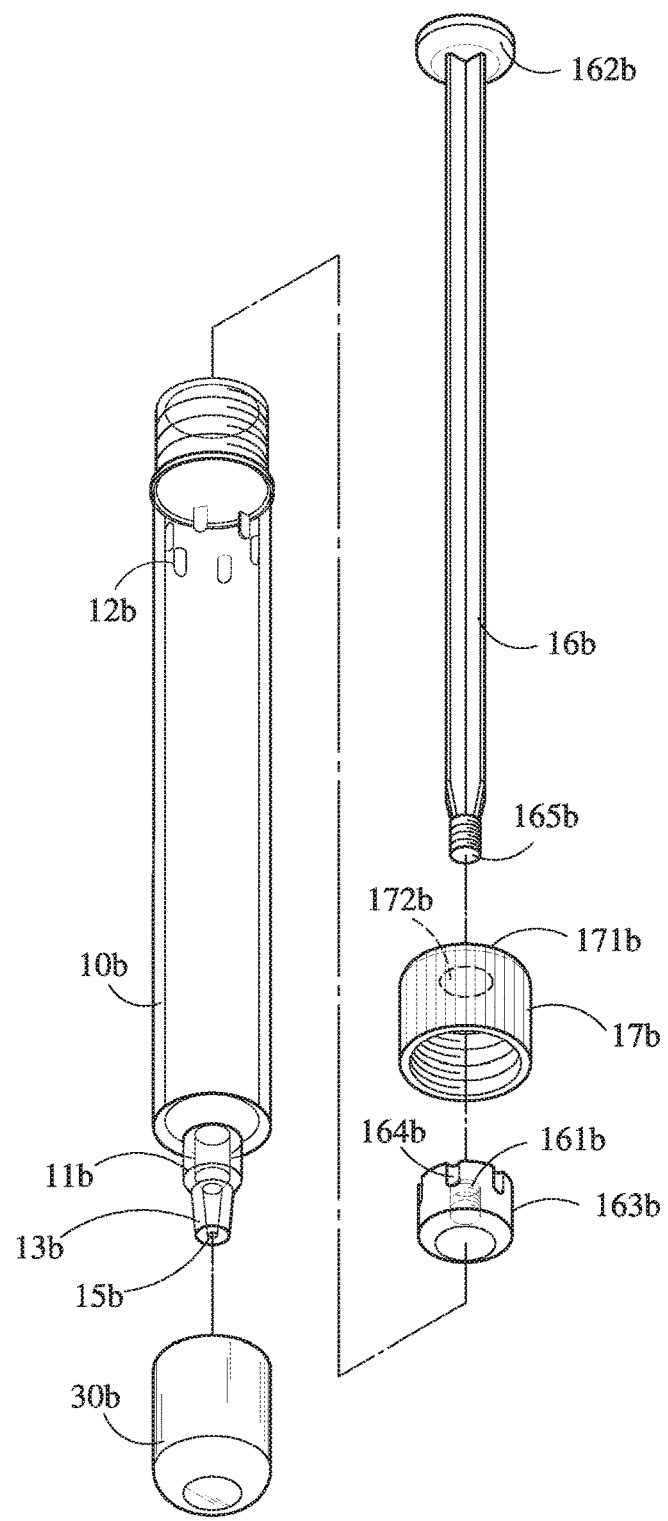
FIG. 7 is an exploded view of a blood sampler in accordance with a second embodiment of the present invention.
Figure 8:
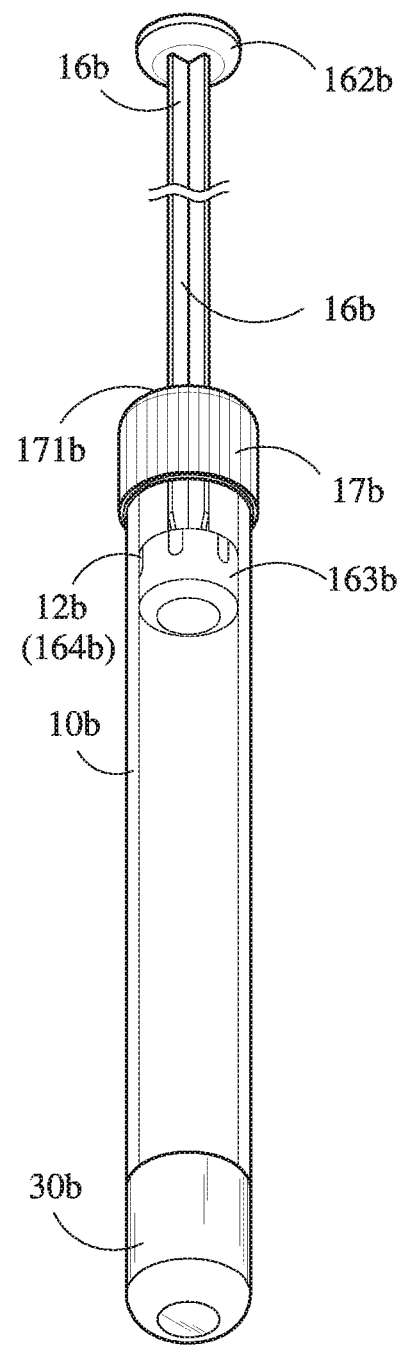
FIG. 8 is an oblique elevational assembly view of the blood sampler in accordance with the second embodiment of the present invention.
Figure 9A:
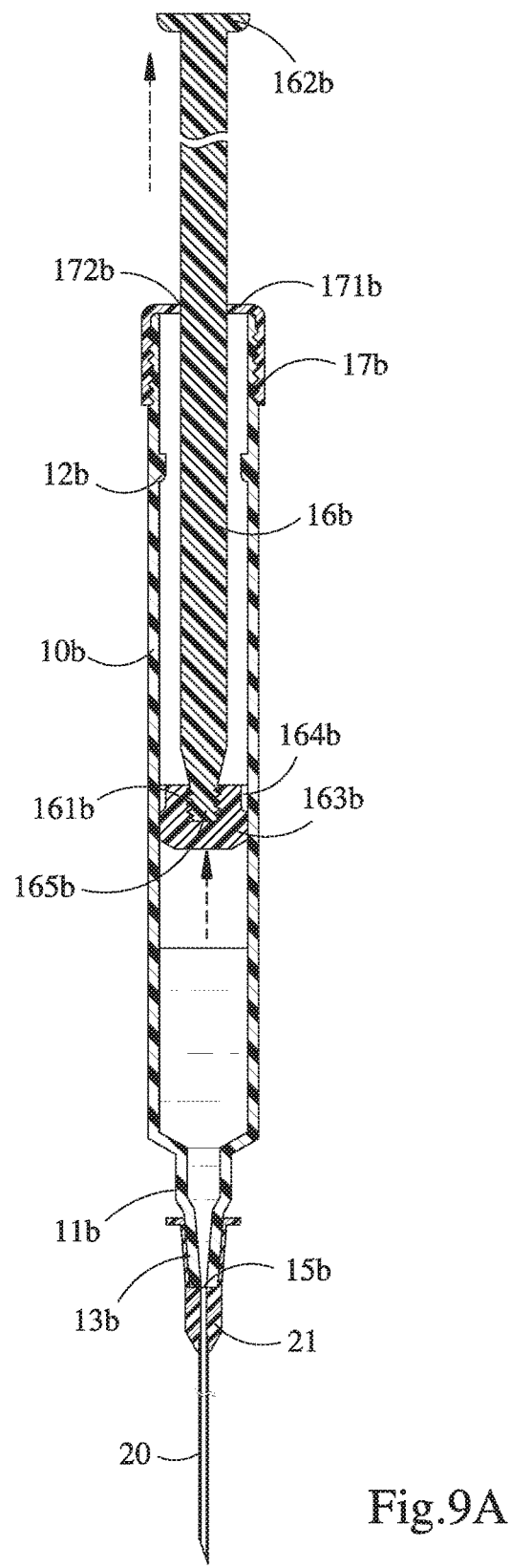
FIG. 9A is a schematic sectional applied view of the second embodiment of the present invention, illustrating a blood sampling operation of the blood sampler.

Referring to FIGS. 7, 8 and 9A, a blood sampler in accordance with second embodiment of the present invention are shown. The blood sampler comprises a hollow transparent barrel 10b, a piston 163b, and a plunger 16b. The hollow transparent barrel 10b comprises a collection portion 11b of reduced diameter axially forwardly extended from a front end thereof and terminating in a coupling portion 13b in reduced diameter, a plurality of longitudinal ribs 12b spaced around an inside wall thereof and disposed near an opposite rear end thereof remote from the coupling portion 13b, two annular stop flanges 14b raised from the inside wall adjacent to the longitudinal ribs 12b, and an outlet 15b axially extending through the collection portion 11b and the coupling portion 13b in communication between the inside space of the hollow transparent barrel 110b and the atmosphere. The hollow transparent barrel 10a further has a piston 163a mounted therein, and a ring cap 17b threaded onto an opposing rear end thereof. The piston 163a is an elastically deformable plastic member axially movably fitted into the inner diameter of the hollow transparent barrel 10a, comprising a screw hole 161a axially disposed in an inner side thereof remote from the coupling portion 13a and a plurality of notches 164 equiangularly spaced around the periphery thereof corresponding to the ribs 12a of the hollow transparent barrel 10a. The ring cap 17b comprises a transverse end wall 171b, and a through hole 172b located at the center of the transverse end wall 171b.

The cap 30b comprises a blind hole 31b adapted for fitting onto the collection portion 11b of the hollow transparent barrel 10b, and a pin 32b located at a bottom end of the blind hole 31b and adapted for fitting into the outlet 15b in the coupling portion 13b to seal the outlet 15b.

The plunger 16b comprises a screw rod 165b located at one end thereof and threaded into the screw hole 161b of the piston 163b, and a thumb rest 162b located at an opposite end thereof for the rest of the thumb for enabling the hand to pull and push the plunger 16b relative to the hollow transparent barrel 10b conveniently and positively.

Figure 9B:
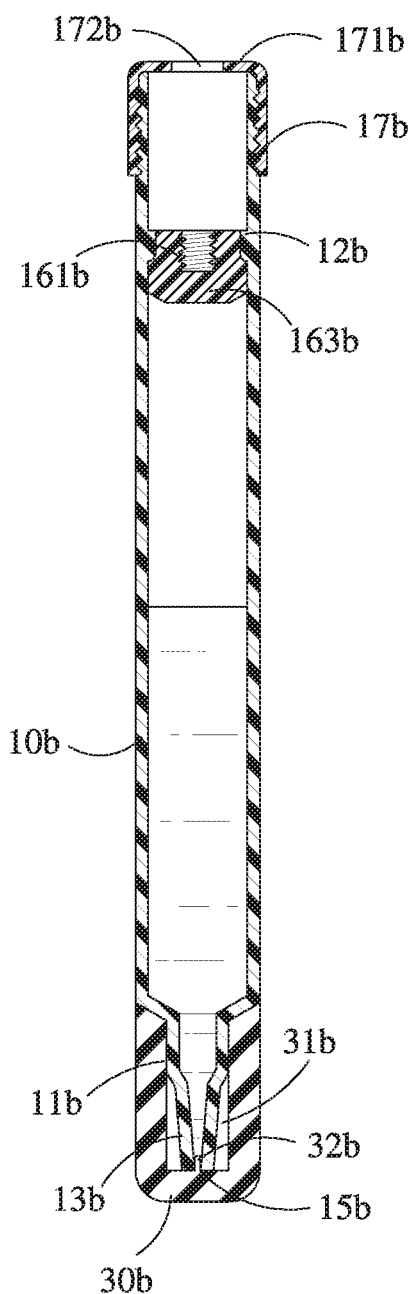
FIG. 9B is a schematic sectional view of the second embodiment of the present invention, illustrating a blood sample collected in the hollow transparent barrel.
Figure 9C:
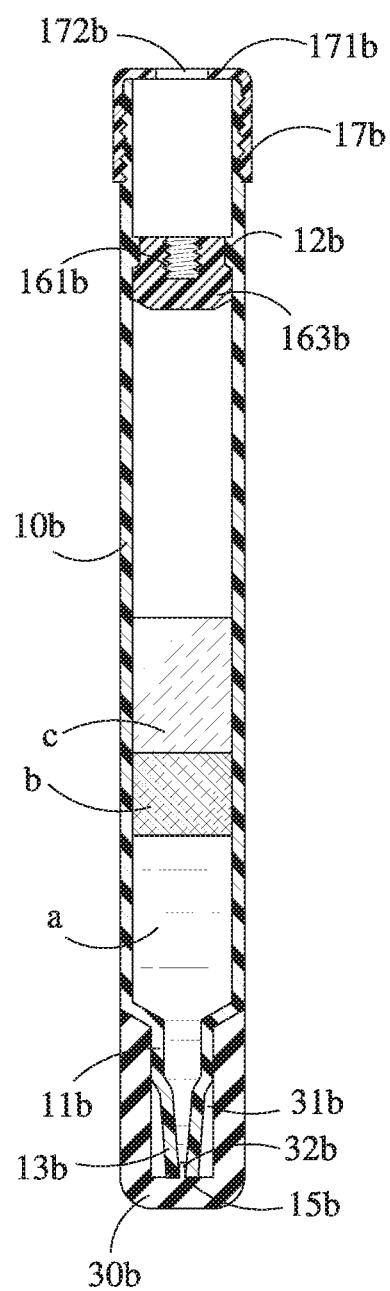
FIG. 9C is a schematic sectional view of the second embodiment of the present invention, illustrating the collected blood sample separated into blood plasma, platelet-rich plasma and serum.

Referring to FIGS. 9B-9E and FIGS. 7 and 9A again, when drawing blood from a patient, separate the ring cap 17b from the hollow transparent barrel 10b, and then insert the piston 163b into the hollow transparent barrel 10b to have the notches 164b of the piston 163b be forced into engagement with the respective ribs 12b of the hollow transparent barrel 10b, and the insert the plunger 16b through the through hole 172b of the ring cap 17b and thread the screw rod 165b of the plunger 16b into the screw hole 161b of the piston 163b, and then attach a hub 21 of a blood collection needle 20 to the coupling portion 3b of the hollow transparent barrel 10b, and then push the thumb rest 162b of the plunger 16b to move the piston 163a forwardly toward the collection portion 11b of the hollow transparent barrel 10b to force the internal air out of the hollow transparent barrel 10b, thereafter, insert the pointed tip of the blood collection needle 20 into the patient's vein, and then pull back the plunger 16a to draw blood out of the patient's vein into the hollow transparent barrel 10b. After a certain amount of blood has been drawn into the hollow transparent barrel 10b, as shown in FIG. 9A, remove the blood collection needle 20 from the patient's body and then cap the cap 30b onto the collection portion 11b of the hollow transparent barrel 10b to force the pin 32b of the cap 30b into the outlet 15b in the coupling portion 13b, and thus, the outlet 15b is sealed. Thereafter, pull the plunger 16b to move the piston 163b backwardly to the position where the notches 164b of the piston 163b are respectively forced into engaged with the respective ribs 12b of the hollow transparent barrel 10b, and then rotate the plunger 16b to disengage the screw rod 165b from the screw hole 161b, thereby separating the plunger 16b from the hollow transparent barrel 10b and leaving the piston 163b in the hollow transparent barrel 10b, as shown in FIG. 9B. Thereafter, put the hollow transparent barrel 10a in a centrifuge with the cap 30a facing down, enabling the blood sample to be separated into blood plasma (a) at the bottom, the ratio of the minimum amount of platelet-rich plasma (b) on the middle and serum (c) in the upper phase, as shown in FIG. 9C, i.e., platelet-rich plasma (b) is suspended between blood plasma (a) and serum (c) and, the amount of platelet-rich plasma (b) is less than the amount of blood plasma (a) and the amount of serum (c)

Figure 9D:
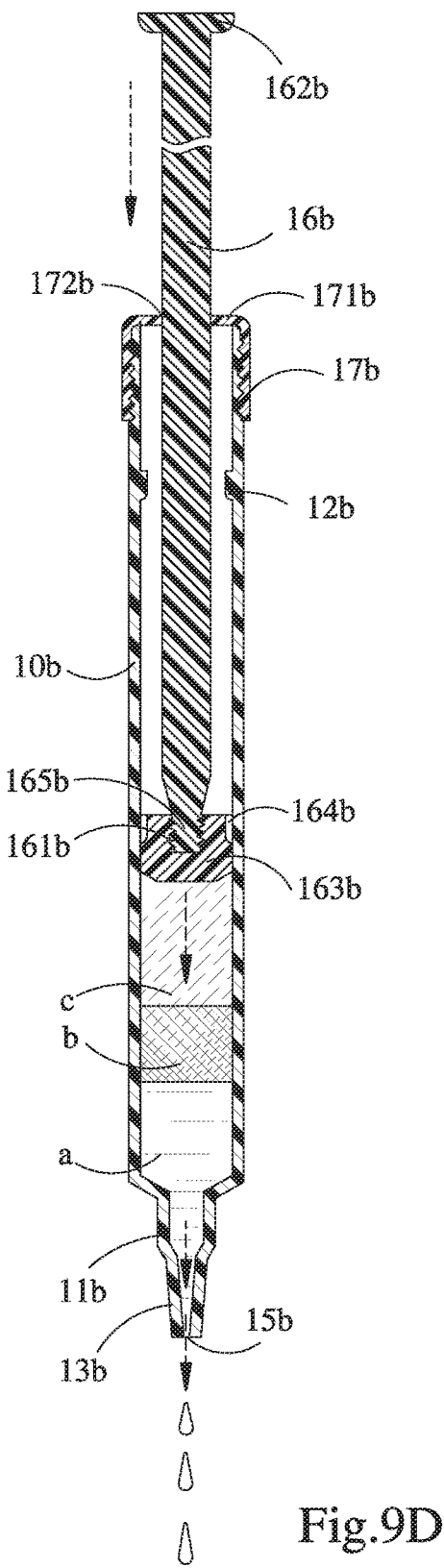
FIG. 9D is a schematic sectional view of the second embodiment of the present invention, illustrating a blood plasma expelling operation status.
Figure 9E:
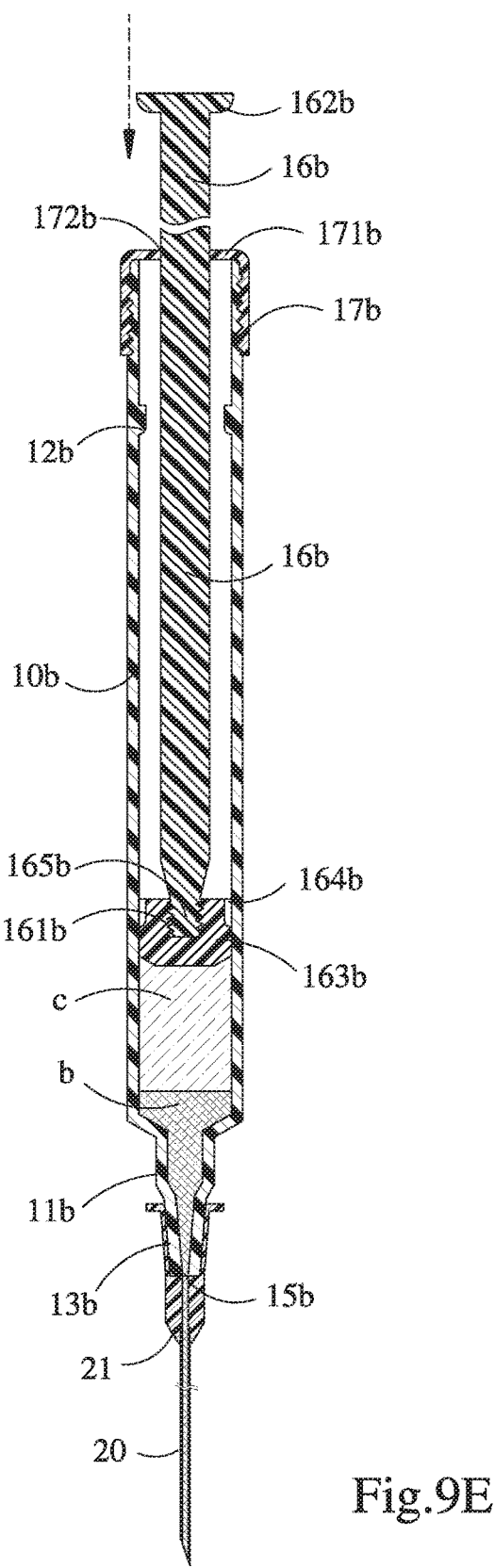
FIG. 9E is a schematic sectional view of the second embodiment of the present invention, illustrating a platelet-rich plasma injection operation status.

When going to inject the collected platelet-rich plasma (b) into an injured area of a patient to help tissues heal, thread the screw rod 165b into the screw hole 161b to connect the plunger 16b and the piston 163b together, and then push the thumb rest 162b of the plunger 16b to move the piston 165b toward the coupling portion 13b to further squeeze the blood plasma (a) out of the hollow transparent barrel 10b, as shown in FIG. 9D, thereafter, attach the hub 21 of a new blood collection needle 20 to the coupling portion 13b of the hollow transparent barrel 10b, and then inject the blood collection needle 20 into the injured area of the patient, as shown in FIG. 9E.

Thus, the hollow transparent barrel 10b can be used as a blood sample container in blood sampling. After a certain amount of blood has been drawn into the hollow transparent barrel 10b, rotate the plunger 16b to separate the plunger 16b from the piston 163b. After separation of the blood collection needle 20 from the coupling portion 13b of the hollow transparent barrel 10b, cap the cap 30b onto the collection portion 11b to force the pin 32b of the cap 30b into the outlet 14b of the coupling portion 13b, sealing blood in the hollow transparent barrel 10b. The hollow transparent barrel 10b can then be used as a test tube and put in a centrifuge for separating the blood sample into blood plasma, platelet-rich plasma and serum. Thus, the hollow transparent barrel 10b can be used as a blood sample container in blood sample collection as well as a test tube for blood sample centrifugation in a centrifuge, avoiding the complicated procedure of using a syringe for blood sample collection and then injecting the collected blood sample from the syringe into a test tube and saving medical supplies.

After the collected blood sample has been separated into blood plasma (a), platelet-rich plasma (b) and serum (c), the bottom serum (c) must be expelled out of the hollow transparent barrel 10b so that the platelet-rich plasma (b) can be accumulated inside the collection portion 11b. In operation, fasten the screw rod 165b of the plunger 16b to the screw hole 161b of the piston 163b, and then push the thumb rest 162b of the plunger 16b to move the piston 163b in direction toward the blood collection needle 20, thereby expelling blood plasma (a) completely out of the hollow transparent barrel 10b and leaving platelet-rich plasma (b) inside the collection portion 11b. Thereafter, attach the hub 21 of the new blood collection needle 20 to the coupling portion 13b of the hollow transparent barrel 10b, and then insert the blood collection needle 20 into the injured area of the patient, and then push the thumb rest 162b of the plunger 16b to inject the platelet-rich plasma (b) out of the hollow transparent barrel 10b into the injured area of the patient. This procedure eliminates the use of another syringe and blood collection needle set to draw the collected platelet-rich plasma (b) out of the hollow transparent barrel 10b and then to inject the platelet-rich plasma (b) into the injured area of the patient, allowing the hollow transparent barrel 10b to be used for collecting blood and injecting collected platelet-rich plasma. Thus, the hollow transparent barrel can be used for collecting blood sample and injecting platelet-rich plasma, and can also be used as a test tube for separating the collected blood sample into blood plasma, platelet-rich plasma and serum, allowing use of one common container in blood sample collection, blood sample centrifugation and platelet-rich plasma injection procedures, and thus, the invention achieves the purposes of simplifying medical procedures, shorting operating time and saving medical equipment.

It's worth mentioning that the invention enables the blood plasma (a) to be expelled out of the hollow transparent barrel 10b before injecting the platelet-rich plasma (b) into the patient. As the platelet-rich plasma (b) is accumulated in the collection portion 11b before injection, the nurse injector can visually check and control the amount of platelet-rich plasma (b) that is injected into the body of the patient, avoiding injection of serum into the body of the patient.

Although particular embodiments of the invention have been described in detail for purposes of illustration, various modifications and enhancements may be made without departing from the spirit and scope of the invention. Accordingly, the invention is not to be limited except as by the appended claims.

What is claimed is:
1. A blood sampler, comprising:
a hollow transparent barrel comprising a collection portion of reduced diameter axially forwardly extended from a front end of a hollow transparent barrel and terminating in a coupling portion in reduced diameter, an outlet axially extending through said collection portion and said coupling portion in communication between the inside space of said hollow transparent barrel and the atmosphere, a plurality of longitudinal ribs spaced around an inside wall of the hollow transparent barrel and disposed near an opposite rear end of the hollow transparent barrel remote from said coupling portion;
a piston press-fitted into the inner diameter of said hollow transparent barrel, said piston comprising a screw hole axially disposed in an inner side of the piston press-fitted remote from said coupling portion and a plurality of notches equiangularly spaced around the periphery of the piston press-fitted and adapted for mating with said ribs of said hollow transparent barrel;
a cap comprising a blind hole detachably press-fitted onto said collection portion of said hollow transparent barrel to seal said outlet; and
a plunger adapted for moving said piston relative to said hollow transparent barrel, said plunger comprising a screw rod located at a front end of the plunger and threaded into said screw hole of said piston, wherein said hollow transparent barrel further comprises a ring cap threaded onto an opposing rear end of the hollow transparent barrel, said ring cap comprising a transverse end wall for stopping said piston inside said hollow transparent barrel and a through hole located at the center of said transverse end wall for the passing of said plunger, wherein the coupling portion is a conical shape.

2. The blood sampler as claimed in claim 1, wherein said hollow transparent barrel further comprises two annular stop flanges raised from the inside wall of the hollow transparent barrel adjacent to said longitudinal ribs for stopping said piston inside said hollow transparent barrel upon backward movement of said plunger to move said piston relative to said hollow transparent barrel.

3. The blood sampler as claimed in claim 1, wherein said cap further comprises a pin located at a bottom end of said blind hole and adapted for fitting into said outlet of said hollow transparent barrel to seal said outlet.

4. The blood sampler as claimed in claim 1, wherein said piston is an elastically deformable plastic member.

5. The blood sampler as claimed in claim 1, wherein said plunger further comprises a thumb rest located at an opposite end of the plunger.

* * * * *